United States Patent [19]

Bainbridge et al.

[11] 4,261,950
[45] Apr. 14, 1981

[54] STERILIZING APPARATUS AND INTEGRATED STERILIZER CONTROL

[75] Inventors: Richard C. Bainbridge, McKean; Ronald P. Krahe, Girard, both of Pa.

[73] Assignee: American Sterilizer Company, Erie, Pa.

[21] Appl. No.: 9,816

[22] Filed: Feb. 6, 1979

[51] Int. Cl.³ .............................................. A61L 2/08
[52] U.S. Cl. ...................................... 422/26; 422/27; 422/28; 422/112; 422/114; 422/116; 422/295
[58] Field of Search .................... 422/111, 26, 27, 28, 422/33, 110, 109, 112, 295, 116, 292, 114; 364/107

[56] References Cited

U.S. PATENT DOCUMENTS

| 3,087,210 | 4/1963 | Neiss | 422/112 |
|---|---|---|---|
| 3,982,893 | 9/1976 | Joslyn | 422/116 |
| 4,067,691 | 1/1978 | McGady | 422/116 |
| 4,127,384 | 11/1978 | Fahlvik et al. | 422/109 |
| 4,149,235 | 4/1979 | Froyd et al. | 364/107 |
| 4,164,538 | 8/1979 | Young | 422/110 |
| 4,165,532 | 8/1979 | Kendall et al. | 364/420 |

FOREIGN PATENT DOCUMENTS

| 207047 | 1/1960 | Austria | 422/292 |
|---|---|---|---|
| 1153490 | 8/1963 | Fed. Rep. of Germany | 422/109 |
| 1342147 | 9/1963 | France | 422/295 |

Primary Examiner—S. Leon Bashore
Assistant Examiner—Michael Goldman
Attorney, Agent, or Firm—Shanley, O'Neil and Baker

[57] ABSTRACT

Sterilizing apparatus and control arrangement providing for selective operation of a plurality of differing types of sterilizing units including sterilizers capable of carrying out a plurality of differing steam and/or gas sterilizing cycles are disclosed. An electronic microcomputer controller is provided on a plurality of circuit boards, at least one of which is an integrated complete controller for at least one type of sterilizer; expander circuit boards extend control to remaining differing types of sterilizers. Also, provision is made for automatically identifying each differing type of sterilizer upon interconnecting an integrated control system with a selected sterilizer.

13 Claims, 9 Drawing Figures

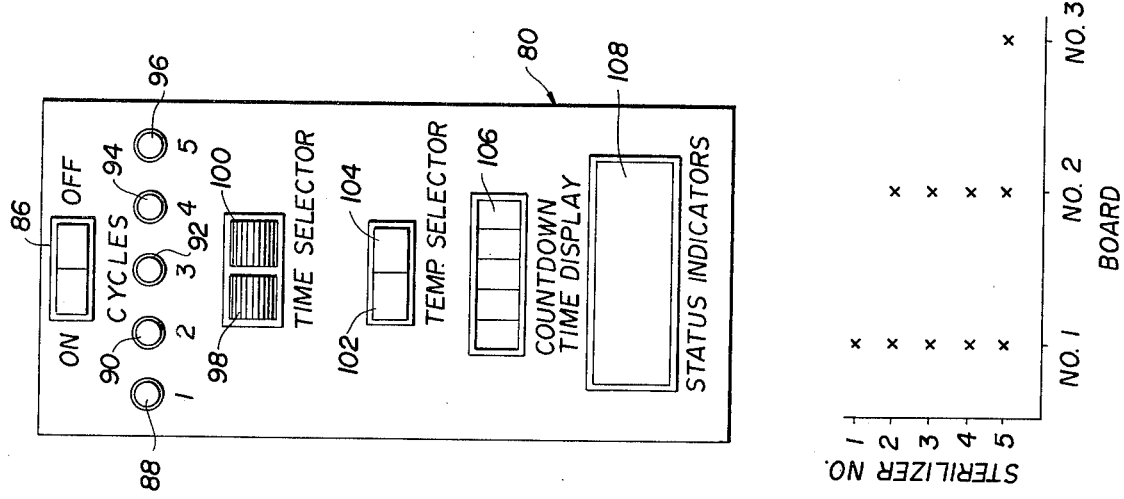
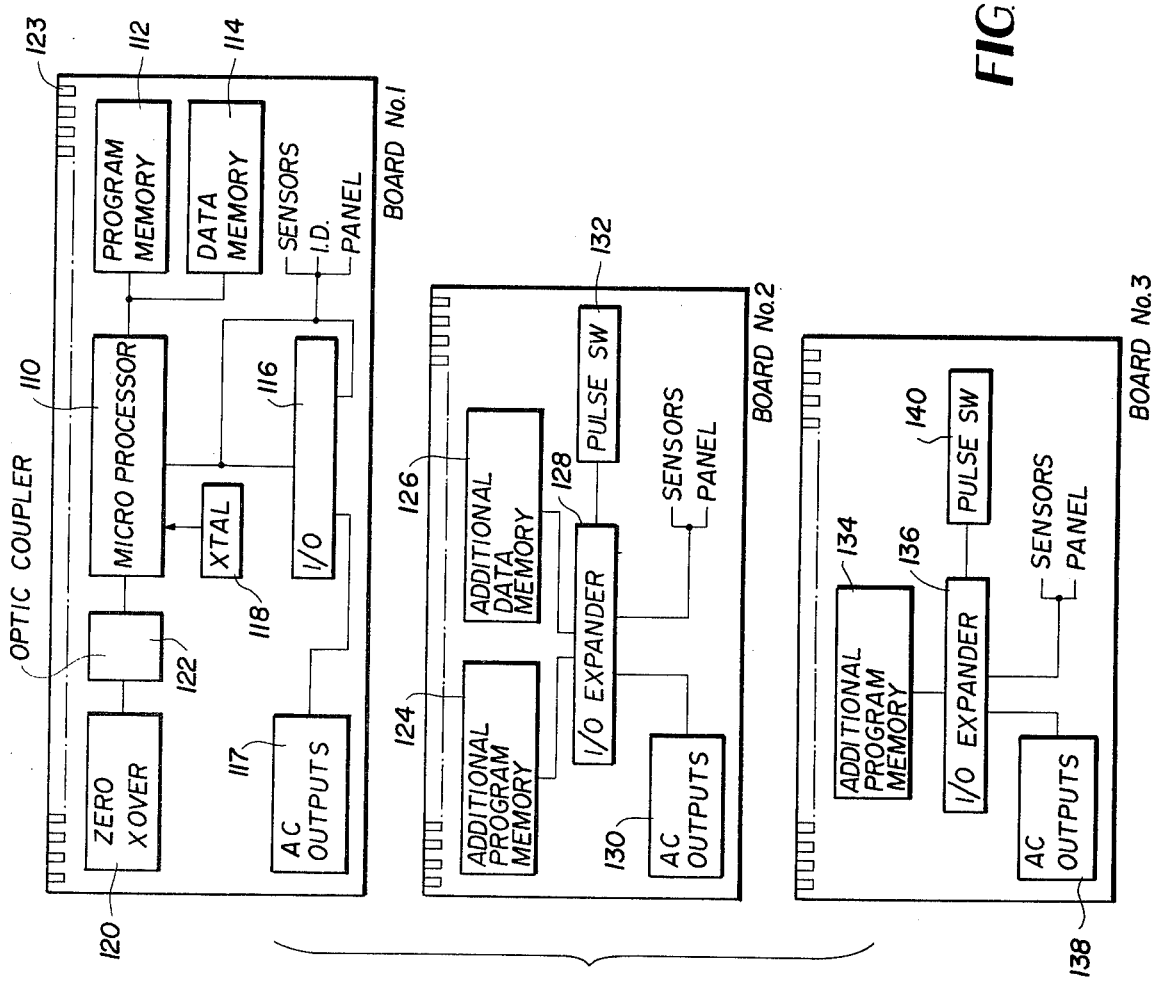

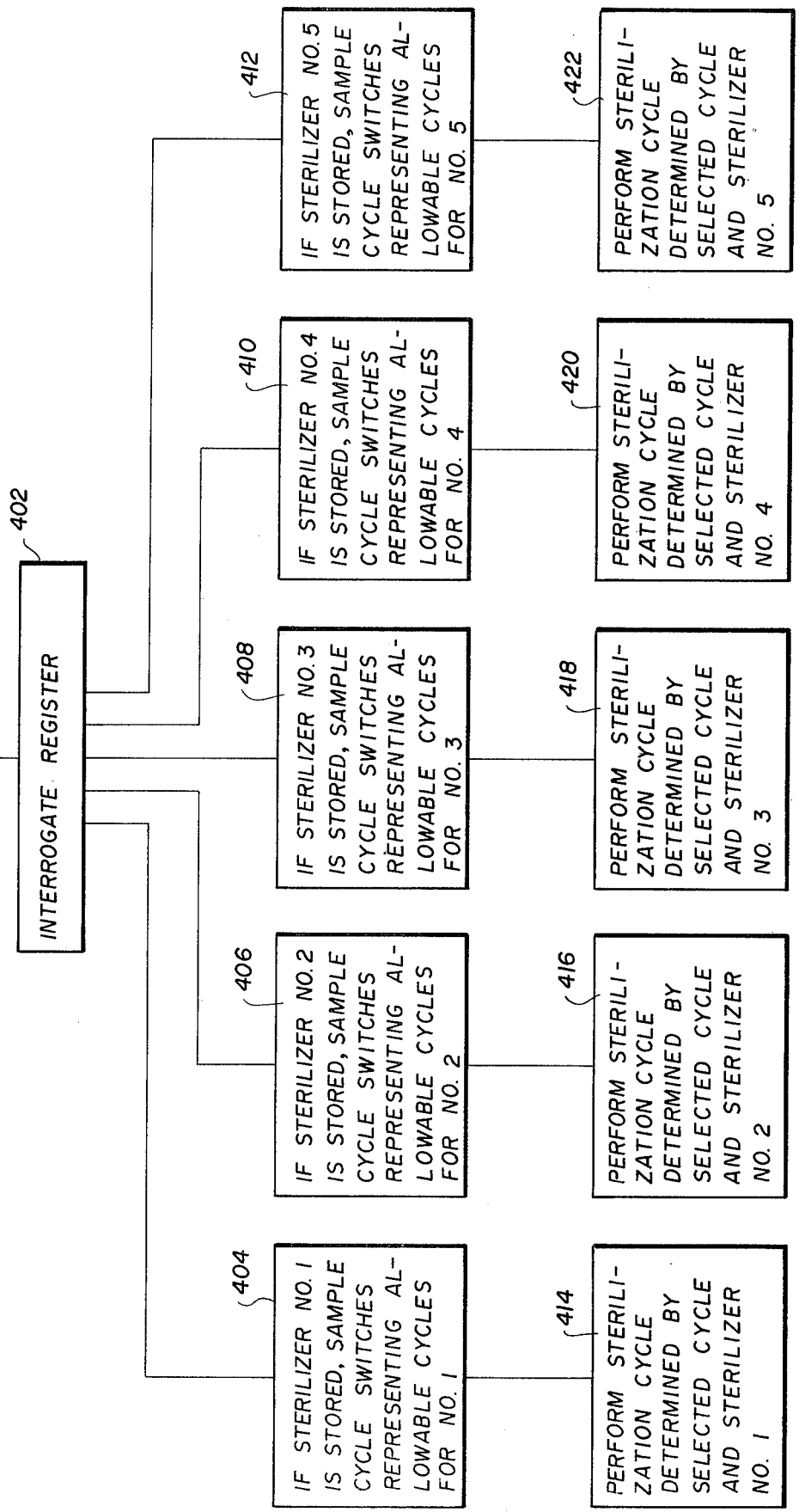

STERILIZING APPARATUS AND INTEGRATED STERILIZER CONTROL

This invention relates to sterilizing apparatus and is concerned with providing for selective operation of a plurality of differing types of sterilizing units including sterilizers capable of carrying out a plurality of differing steam and/or gas sterilizing cycles. More particularly, the invention is concerned with providing for sterilizer identification as well as selection and operation of cycles through an integrated control system.

In conventional operation of hospital and industrial sterilizing apparatus, a single chamber can be used at differing times for a steam cycle or a gas (ethylene oxide) cycle but separate control panels and separate circuit means were required for each cycle. Also, separate control arrangements have been required for each differing sterilizer which performed either steam or gas cycles. Such separate control arrangements can occupy space equivalent to that provided for certain hospital type sterilizers. However, greater disadvantages are inherent in the inventory and service requirements of such practice and in the complexity resulting from unnecessary duplications.

Long available miniaturizing developments in electronics, including microprocessor technology, can be used to reduce space requirements but, prior to the present invention, the sterilizer art has been limited to the separate control approach described so that the more significant benefits of such electronic development could not be realized.

A basic and significant departure from prior sterilizer art and practice of the present invention involves the concept of integration of electronic control apparatus to enable selective control of a plurality of sterilizers and to further enable selection and operation of differing combinations of sterilizing cycles on the various sterilizers. Economic and operational advantages result from this integrated control concept in manufacture, service and operation of sterilizers.

The invention provides an integrated control system in which the same control apparatus is used to selectively control a plurality of different types of sterilizing units, each of which can perform a differing sterilizing cycle or a differing combination of sterilizing cycles. For practical purposes, it is desirable to provide for optimum selectivity from a reasonable number of differing types of sterilizing units; e.g. a sterilizer capable of performing differing steam cycles, a sterilizer capable of sterilizing liquids, a sterilizer capable of sterilizing liquids and performing another steam cycle, a sterilizer capable of performing differing gas cycles, and a sterilizer capable of performing selected steam and gas sterilizing cycles.

Basic steam cycles vary in conditioning methods, e.g. gravity flow vs. evacuation and, in sterilizing phase steps dependent on the goods, e.g. liquids vs. fabrics. Gas cycles can vary basically in conditioning methods and temperature of operation. Considering the needs of various hospitals and the needs of various areas within a hospital, several basic cycles are selected which will satisfy most requirements. Each differing type of sterilizer is arranged to perform one or, to selectively perform more than one, of the basic sterilizing cycles to permit optimum matching of a particular type of sterilizing unit to needs at a particular installation. The integrated control system of the present invention provides for operation of any of the differing types of sterilizing units offered and also provides for selection and operational control of the cycles available on a particular sterilizing unit.

Among other factors, sterilizing needs serve the function of limiting the number of practical combinations of cycles and the number of practical types of sterilizing units. Selection from five differing types of sterilizing units, with various embodiments of five sterilizing cycles, will be utilized in describing the principles of the invention although other combinations can be made utilizing the present teachings.

A significant contribution of the invention is the provision of integrated electronic control apparatus which is arranged to operate interchangeably with any of the differing types of sterilizers. In addition, provision is made for each differing type of sterilizer to be self-identifying to such control apparatus.

Other advantages and contributions of the invention will be brought out in a more detailed description of the invention as represented in the accompanying drawings.

In the drawings:

FIG. 2 is an exemplary embodiment of a control panel utilized in the invention;

FIG. 3 is a schematic presentation of circuit board control apparatus of the invention, depicting a representative circuit board layout;

FIG. 4 is a chart illustrating circuit boards utilized to operate differing types of sterilizers in accordance with the invention;

FIG. 9 is a flow chart which depicts the operation of the cycle identification feature of the apparatus of the invention.

Figure 1:
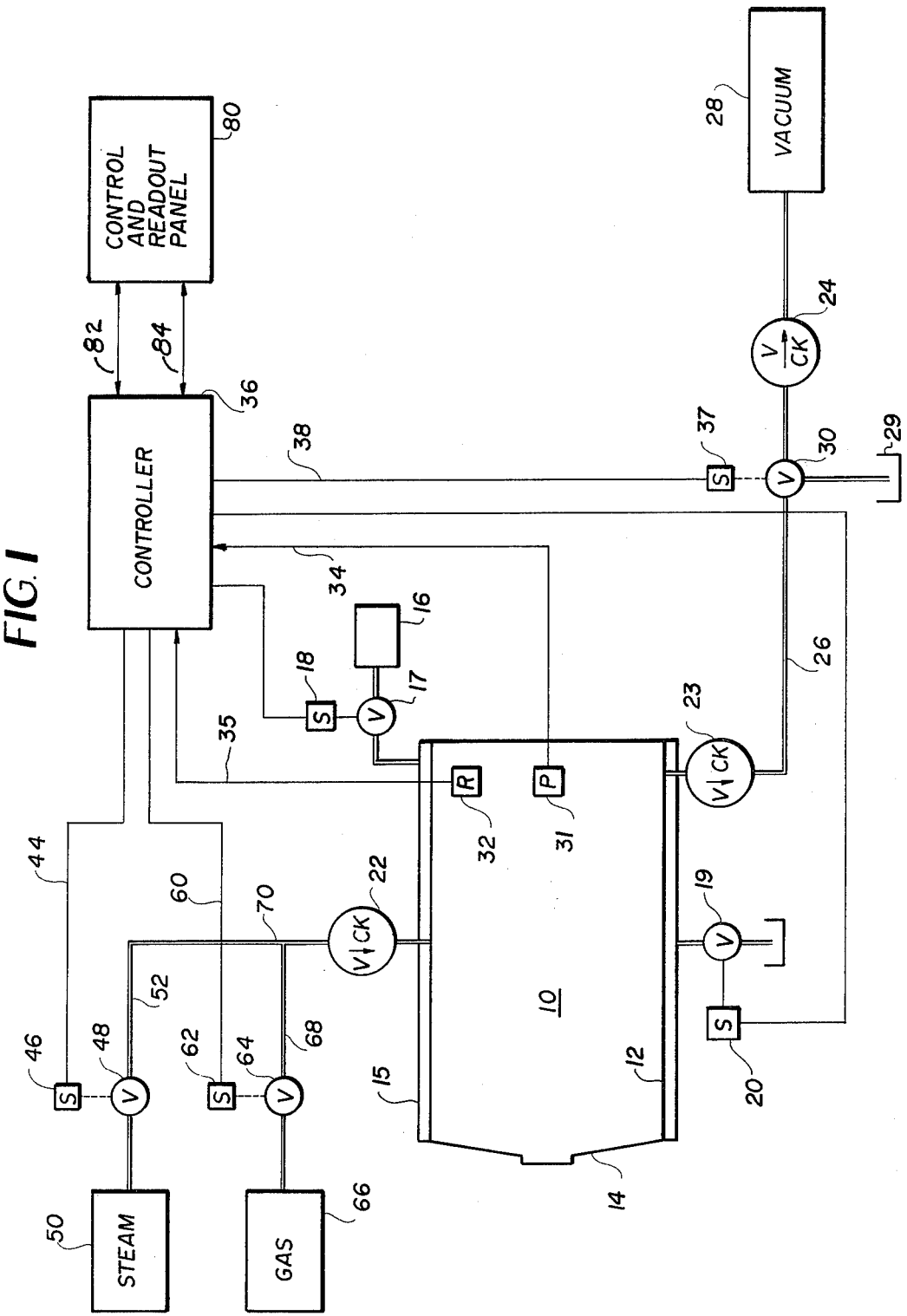
FIG. 1 is a schematic illustration of sterilization apparatus for carrying out the invention.

A single chamber 10 is shown in FIG. 1 with a composite of various conduits and other elements which will be referred to in describing differing sterilizers. As will be readily understood, a gas source and gas conduits would not be part of a sterilizer offering only steam cycles. Also, other chamber wall heating means, such as insulation and electrical strip heaters, could readily be substituted for a chamber jacket.

Chamber 10 is defined by shell 12 and closure 14. A jacket 15 can surround a major portion of the chamber walls and can be supplied with a temperature control fluid from source 16 through valve 17 under the control of solenoid 18; jacket 15 is drained through valve 19 under the control of solenoid 20.

Check valve 22 is provided in the supply line to the chamber and check valves 23 and 24 in the exhaust line 26. The chamber 10 can be exhausted through vacuum source 28 or drain 29 at valve 30.

Chamber conditions can be sensed by pressure sensor means 31, or other sensing means 32 where applicable. Chamber temperature at various levels is the only chamber condition to be sensed for many cycles. Sensor 32 can, for example, be located as a wall temperature sensor or a drain line temperature sensor, or sense other conditions when required by a particular cycle. Pressure sensor 31, which can comprise a plurality of pressure switches, is connected through electrical signal line 34 and, sensor 32 is connected through line 35, to controller 36.

Solenoid 37 for exhaust valve 30 is connected to controller 36 by line 38. Similarly, the solenoid control valves on the chamber supply lines are connected to controller 36; line 44 is connected to solenoid 46 for steam valve 48 which controls flow from source 50 in conduit 52. Line 60 to solenoid 62 for valve 64 controls flow of biocidal gas from source 66 in gas conduit 68. Steam conduit 52 and gas conduit 68 are directed through common conduit 70 into chamber 10.

A control and read-out panel 80 is connected to controller 36 by electrical conductors 82, 84 which electrically transmit information between controller 36 and the control and read-out panel 80. For example, selections of sterilizing parameters selected at panel 80 are transmitted to controller 36 and, monitored cycle information is transmitted from controller 36 to read-out panel 80 for display. On/off switch 86 is mounted on the control and read-out panel 80.

Switches 88, 90, 92, 94, and 96, shown on the control and read-out panel 80 in FIG. 2, are provided for selecting from representative sterilizing cycles numbered "1" through "5". With the advantages provided by the integrated control concept of the invention, a single design for the control and read-out panel 80 is provided for all of the plurality of differing type sterilizers which can be controlled. Selective lighting brought about by the integrated control displays only information and data pertinent to the particular sterilizer. Since all of the types of sterilizers which could be operated by controller 36 will not be capable of performing all of the five cycles, operator selection of the numbered cycles is limited to those which can be carried out by the particular type of sterilizer in which controller 36 is mounted. As described in greater detail below, a microcomputer controller automatically prevents selection of cycles which could not be performed on the particular type of sterilizers to which the microcomputer controller is connected.

Other controls provided on panel 80 are time selector switches 98 and 100 for selecting the sterilization and dry times in the case of a steam cycle and the sterilization time in the case of a gas cycle. Temperature selection means 102 and 104 are provided for selecting the temperature of gas sterilization cycles.

The display means on the panel preferably includes countdown time display means 106 for digitally displaying the time remaining in a cycle phase. Additionally, status indicator lamps 108 are present to provide the operator with a current indication of the part of the cycle being carried out as well as to provide warning indications.

An important feature of the present invention is the provision of a microcomputer control means for interchangeable use in a plurality of different types of sterilizers for controlling a number of different sterilizing cycles. In accordance with the present invention, an integrated approach to sterilizer control is employed in which integrated circuit board means, which can include a small number of circuit boards, may be used interchangeably in all of the differing types of sterilizers. The microcomputer is programmed so that, upon appropriate selection, it can control performance of any of the cycles which can be performed on any of the sterilizers. In the integrated circuit board approach, microcomputer, low-level input/outputs, and D.C. and A.C. drivers are provided on a single circuit board. This circuit board, identified as board #1, is complete in itself so as to be capable of operating at least one type of sterilizer. To operate other types of sterilizers which perform more complex cycles or a greater number of different cycles, "expander" boards are provided which have additional memory capacity as well as additional input/output and driver capacity. When these additional boards are operated in conjunction with the first board, they effectively expand the control unit of the first board to accomplish more complex control.

This integrated circuit board concept with expander boards results in efficient use of components since the total number of components used when one, or more than one board is used, is approximately matched to the number of components needed for desired control. Since the boards are programmed to interchangeably operate with all types of sterilizers, integrated circuit board #1 is the same on all sterilizers. As a result, maintenance is substantially simplified, inventory items reduced, and fewer drawings need to be maintained. For instance, circuit board #1 is interchangeable in all types of sterilizers; if one type of sterilizer in a hospital malfunctions because of a fault in board #1, the identical board from another type of sterilizer in the hospital can replace the faulty board temporarily until a new board can be obtained; or, a single spare part, e.g. circuit board #1, is a spare for all the differing types of sterilizers in a hospital.

FIG. 3 is an exemplary illustration of the circuit board organization using three circuit boards. Board #1 is a complete controller for independently and completely controlling the operation of at least one type of sterilizer; circuit board #1 includes microprocessor 110 which operates in conjunction with program memory 112 and data memory 114. The microprocessor 110 also cooperates with input/output means 116 which receive the D.C. sensor signals, input signals from panel 80, and a sterilizer identification signal. Other units pictorially depicted on board #1 are A.C. output unit 117 for controlling the solenoid valves, clock-controlling crystal 118, a zero crossover network, and optic coupler 120 and 122 respectively. Electrical contact lands generally indicated by reference numeral 123 are disposed along one edge of the board for external electrical connection.

Board #2, illustrated in FIG. 3, includes expander components including additional program memory 124, additional data memory 126, input/output expander 128, and A.C. output unit 130. Board #3 includes further expander components such as additional program memory 134 and input/output expander 136.

Utilization of the circuit boards of FIG. 3 is depicted in the exemplary chart of FIG. 4 in which the sterilizer types are represented along the ordinate, and the numbered, printed circuit boards are represented along the abscissa. Each different sterilizer type is capable of performing a different sterilization cycle or combination of sterilization cycles. Sterilizer #1 is controlled by a circuit board #1; the controller for sterilizers #2, #3, and #4 comprise circuit boards #1 and #2 in combination; and, the controller for sterilizer #5 comprises boards #1, #2, and #3 in combination. Advantages of this utilization reside in the close matching of components provided to needs.

It is to be understood that the allocation of printed circuit boards shown in FIG. 4 is exemplary only; for instance, a circuit board could be expanded to operate more than one sterilizer or to permit more than four sterilizers to be operated with two circuit boards. Further, it is to be understood that three circuit boards are shown for purposes of illustration only, and that a fewer or greater number as required may be used to control all sterilizers while still utilizing the integrated concept of the invention in which the same printed circuit board and control components are used in a plurality of different types of sterilizers.

Figure 5:
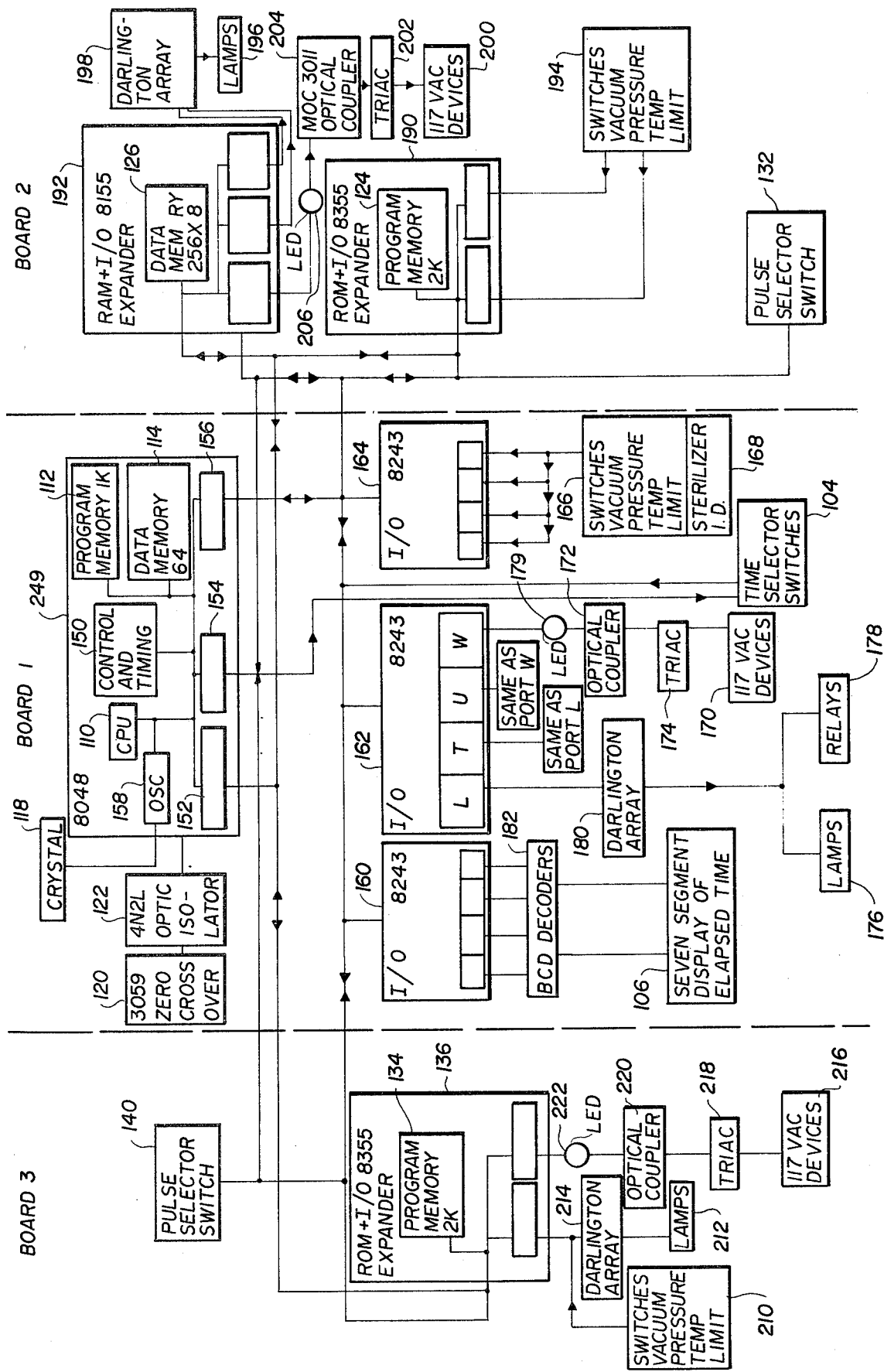
FIG. 5 is a block circuit diagram of the circuit boards of FIG. 3.

FIG. 5 is a detailed block diagram of the electronic microcomputer controller shown schematically in FIG. 3 and, like FIG. 3, shows the division of components onto discrete circuit boards. In general, the microcomputer control means includes central processing unit 110 which operates under the direction of control and timing unit 150 to process information which is stored in program memory 112, which is a read-only memory (ROM). Memory 112, which is non-volatile, and preferably is of the semi-conductor type, contains a stored program or series of instructions for controlling the performance of any selected sterilization cycle which may be performed by any one of the sterilizers. Additionally, data memory 114 is provided and is used for the temporary storage of data, including such data as that pertaining to which type of sterilizer the computer is controlling, and data representative of the countdown time displayed by display means 106 on panel 80.

Communication to and from the microcomputer is by way of ports 152, 154 and 156, and the timing base is provided by oscillator 158, the frequency of which is controlled by crystal 118. The actual microcomputer chip utilized may, by way of example, be an Intel 8048.

Zero crossover network 120 is coupled to the microcomputer through optic isolator 122. A single zero crossover network 120 provides zero crossover interfacing with all of the many A.C. switches utilized.

To increase the input/output capacity of the microcomputer in circuit board #1, input/output augmenting means 160, 162, and 164 are provided. In general, the inputs are signals from the chamber condition sensors, limit (door closure) transducers, and the sterilizer identification signal, to be described below. One set of outputs are signals for the triacs for completing A.C. circuits to operate the valve-controlling solenoids shown in FIG. 1 to selectively control the flow of fluid to the chamber; another set of outputs are signals for activating the display means and indicator lamps disposed on control and read-out panel 80, shown in FIG. 2. Thus, in FIG. 5, input augmenting means 164 receives inputs from pressure, temperature and limit transducers at 166 and from the sterilizer identification unit at 168. Output augmenting means 162 provides outputs to the solenoids 170 through optical isolator means 172 and triac means 174. Output means 162 provides for further outputs to the lamps 176 and relays 178 of control panel 80 through Darlington driver array 180, while output means 160 provides outputs to the countdown display means 106 of the panel through binary coded decimal (BCD) decoders 182. The outputs of time selector switches 104 on panel 80 may be coupled directly to port 154 of the microcomputer. Light-emitting diodes such as 179 are provided for testing the operation of the circuit board.

Additional program memory 124 in association with input/output expander 190, and additional data memory 126 in association with expander 192, are provided on board #2. The pressure, temperature and limit transducer input signals shown at 194 are inputs to the ports of expander 190 while the output signals to panel lamps 196 and to the A.C. operated solenoid devices 200 are provided by expander 192. Further, the input from the pulse selector switch 132 for selecting the number of conditioning steam pulses is provided to port 154.

In similar fashion, board #3 includes additional program memory 134 in association with expander 136 which accepts transducer inputs 210 and provides outputs to the A.C. voltage device 216 and lamps 212; selector switch 140 may be coupled to port 154. The input/output expander chips may be Intel 8243's. The program memory expander chips Intel 8355's and the data memory expander chips Intel 8155's.

Figure 6:
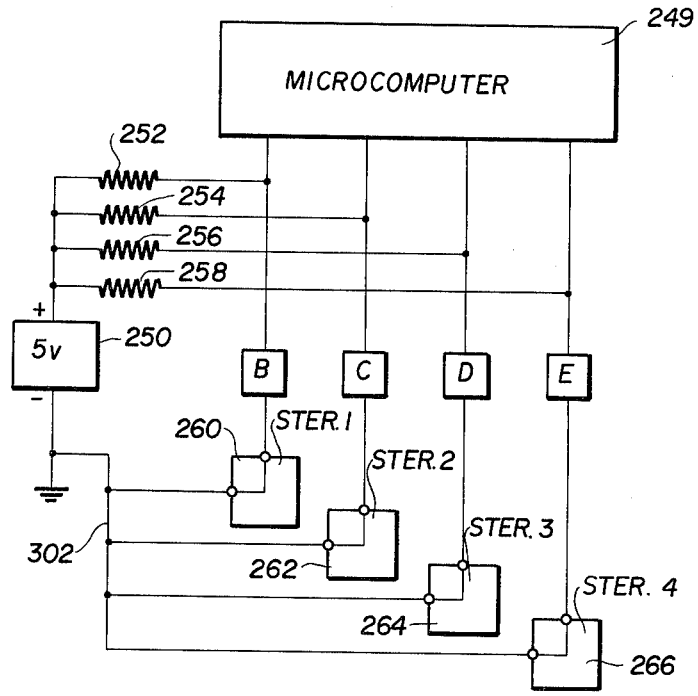
FIG. 6 is a circuit diagram embodying the sterilizer identification feature of the invention.

An important contribution of the present invention is the sterilizer identification feature and an illustrative embodiment of a circuit for accomplishing such identification is shown in the schematic diagram of FIG. 6. As explained above, the same basic controller is used interchangeably in a number of different types of sterilizers and is programmed to encompass all cycles, so that appropriate selection by the operator causes the controller to carry out the cycle selected. However, the same cycle may be performed somewhat differently depending on the type of sterilizer which is being operated. For instance, a cycle for sterilizing liquids may involve a differing sequence of steps in a sterilizer using gravity to remove air from the chamber then in one using vacuum evacuation. Further, the differing sterilizer types, because of the different physical makeup of each type, may require different preparatory steps to be performed before a cycle is begun.

In accordance with the present invention, a sterilizer automatically identifies itself to the controller when a circuit board is connected to that sterilizer. The sterilizer "tells" the controller which type of sterilizer it is in, so that the proper part or parts of the program may be established for performing the appropriate cycle steps for the particular sterilizer type.

The identification system provides means on the sterilizer, differing for each sterilizer type, which cooperate with the controller when connected to the sterilizer.

Referring to FIG. 6, elements B, C, D, and E are lands or input terminals to circuit board #1 shown in FIGS. 3 and 5. Microcomputer 249, on circuit board #1, is arranged to sample lands B, C, D, and E, and to identify the sterilizer type dependent on which one of the lands carries a signal. The positive side of D.C. voltage supply 250 is connected through resistors 252, 254, 256, and 258, respectively, to lands B, C, D, and E. If the microcomputer controller is located in sterilizer type #1, then land B is connected to ground through a permanent connection 260 of sterilizer #1. Similarly, if the computer controller is in one of sterilizer types #2, #3, or #4, then one of lands C, D, or E, respectively, is connected to ground through a permanent one of connections 262, 264, or 266, respectively, of the sterilizers. Therefore, when circuit board #1 is in sterilizer type #1, lands C, D, and E are at +5 volts potential since there is no closed circuit path (connections 262, 264, and 266 are not made) across the voltage supply which includes any of lands C, D, and E. Land B, however, is at ground potential, there being a complete circuit loop through land B and connection 260, which causes current to flow through resistor 252. This identifies sterilizer #1. Similarly, if the circuit board were mounted in one of the sterilizers types #2, #3, or #4, then one of lands C, D, or E, respectively, would be at ground potential, thus identifying a particular sterilizer. If none of the lands is at ground potential, sterilizer #5 is identified. In the case of the "ground identification" embodiment illustrated in FIG. 6, ground potential is the "signal" detected.

Figure 8:
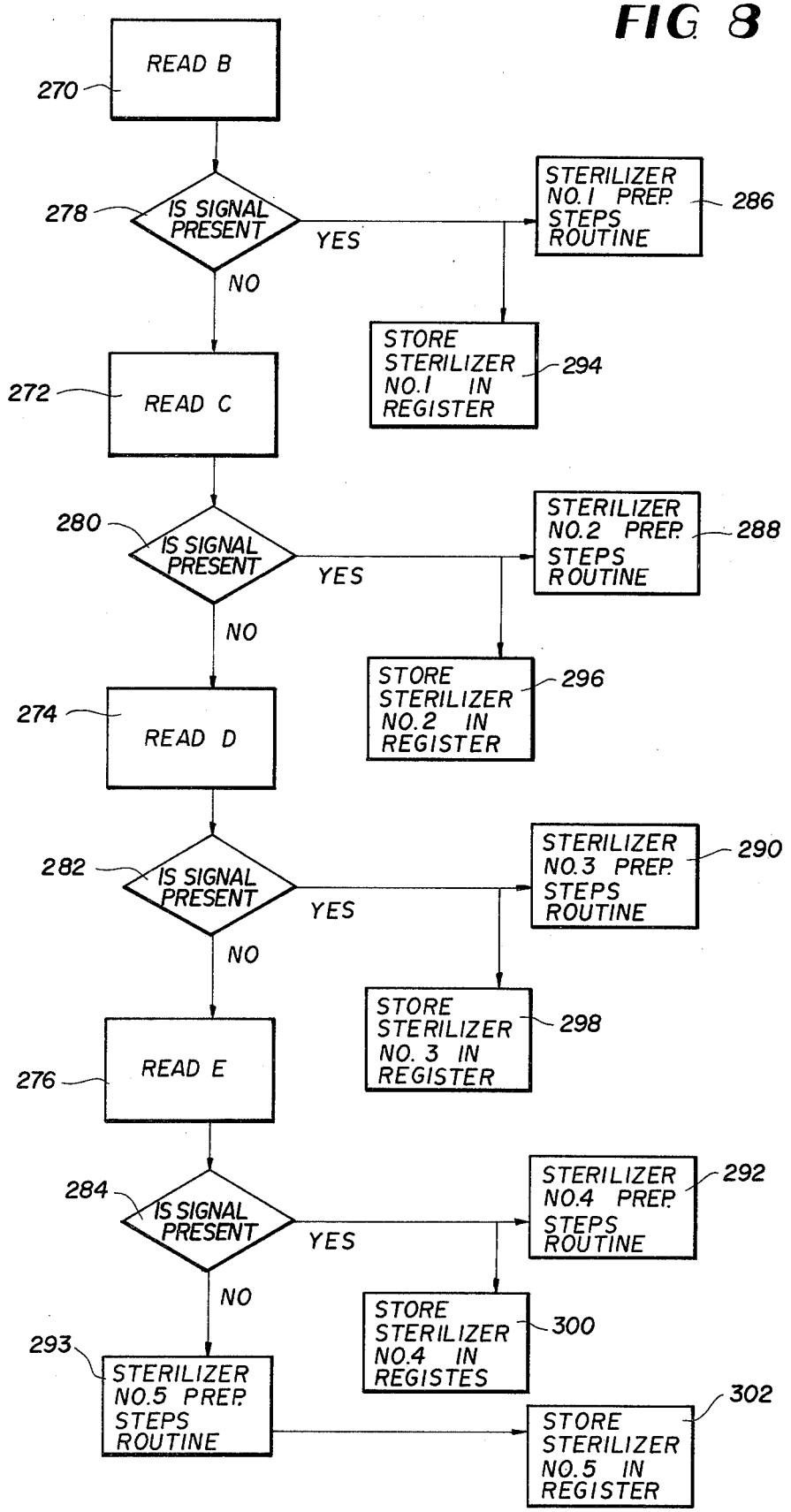
FIG. 8 is a flow chart which depicts the operation of the sterilizer identification feature of the invention.

FIG. 8 is a flow chart which further clarifies the operation of the ground identification circuit of FIG. 6. Thus, after the start signal occurs, lands B, C, D, and E are successively read as represented at blocks 270, 272, 274, and 276. A determination is made as to whether the signal is present at any of the lands at blocks 278, 280, 282, and 284 and, if so, then a corresponding sterilizer is identified, as shown at blocks 286, 288, 290, and 292. If a signal is not present at one of B, C, D, or E, then sterilizer #5 is identified at block 293. At the time that the sterilizer identification is made, the identity is stored in a register, as represented at blocks 294, 296, 298, 300, and 302.

It should be understood that the "ground identification" circuit illustrated in FIG. 6 is a specific embodiment of a system which effects sterilizer identification through cooperation of the controller and separate means in each differing type of sterilizer; other arrangements involving cooperation with differing permanent electrical connections or structures at the sterilizer can be devised based on the above disclosure.

Figure 7:
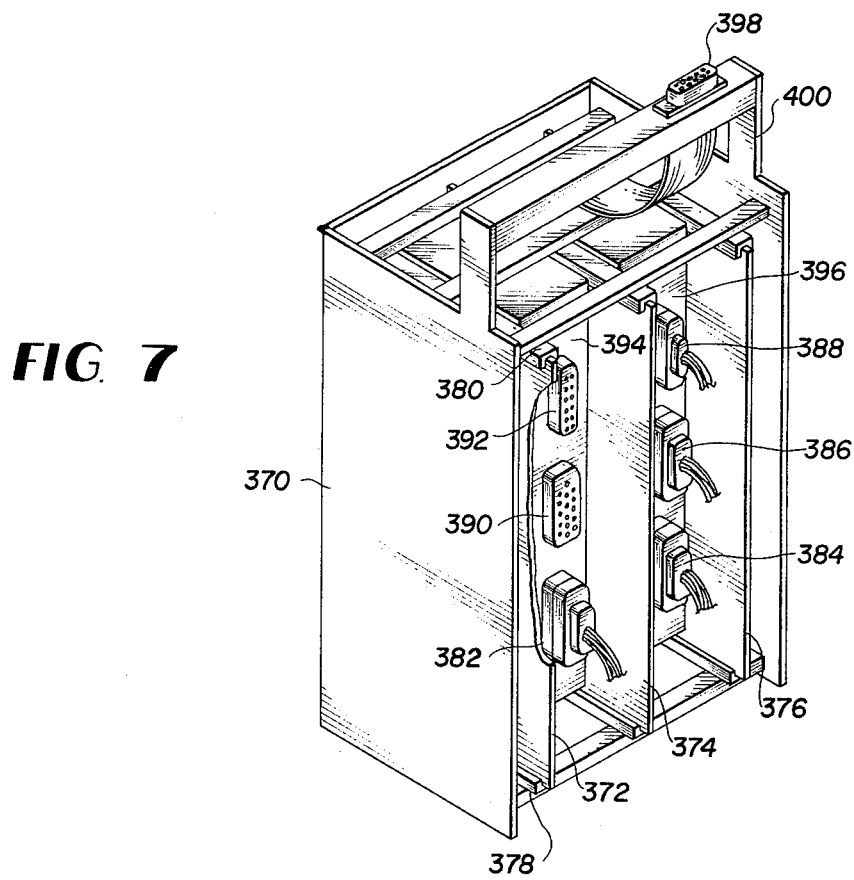
FIG. 7 is a perspective view of housing means for sterilizer mounting of circuit boards.

FIG. 7 illustrates a housing for mounting the circuit boards. U-shaped 370, which has two sides and a back, houses circuit boards 372, 374, and 376, which may correspond to the circuit boards #1, #2 and #3 discussed above. To achieve the advantages of standarization, all of the differing types of sterilizers may be constructed so as to receive the same U-shaped housing 370.

The boards may be secured in the housing by any known mechanical means. For instance, circuit board 372 is held by elongated, parallel, groove members 378 and 380; loading clips can also be added.

To permit the circuit boards to be removed from the housing and to permit the housing to be removed from the sterilizer, a plug and socket arrangement is used. Thus, a wire is connected to each of the lands of the circuit boards, and the wires are terminated in a plurality of plugs, such as plugs 382, 384, 386, and 388. A plurality of sockets such as 390 and 392 are disposed on mounting plates 394 and 396 which extend perpendicular to the orientation of the printed circuit boards. If desired, an additional socket or sockets may be mounted on an external member, such as socket 398 which is mounted on inverted U-shaped member 400. After the housing 370 is positioned in its receptacle in the sterilization apparatus, wires from various components of the sterilizer such as the valve-operating solenoids and the condition sensors are connected with the plugs. The plugs are then inserted into the sockets, thus completing connection of the printed circuit boards to the sterilizer.

FIG. 9 is a flow chart illustrating how the microcomputer determines which cycle the sterilizer is to perform. As discussed above, at the time that the identification is made, the identity of the sterilizer is stored in a register, as shown at blocks 294, 296, 298, 300, and 302 of FIG. 8. In the cycle selection routine illustrated in FIG. 9, that register is first interrogated as represented at block 402, to determine the identity of the sterilizer. Since not every cycle which can be selected by the cycle selection switches on panel 80 can be performed by every sterilizer, the microcomputer is arranged to sample only those switches which can select allowable cycles for the particular sterilizer which the microcomputer is in. Thus, as represented by block 404 in FIG. 9, if the interrogation of the register indicates that sterilizer #1 has been identified, the cycle selection switches representing allowable cycles for sterilizer #1 are sampled. If sterilizer #2 is identified, then the cycle selection switches representing allowable cycles for sterilizer #2 are sampled as represented at block 406, and so on for the other sterilizers as represented at blocks 408, 410, and 412.

The actual sterilization cycle performed is determined by both the cycle selected at panel 80 and the type of sterilizer which is being operated. For example, as discussed above, steps of a liquid sterilizing cycle may differ when a sterilizer using gravity air removal than when performed by a sterilizer using a vacuum source. In FIG. 9, the performance of the proper cycle steps as determined by both the cycle selected and the sterilizer type is represented at blocks 414, 416, 420, and 422.

While specific mechanical structure, electrical elements, and values have been set forth for purposes of describing, it should be understood that modifications can be made in these specifics while utilizing basic principles and contributions of the invention. Therefore, in analyzing the scope of the present invention, reference should be made to the accompanying claims.

We claim:

1. Sterilizing apparatus having a microcomputer control arrangement providing for selective operation of a sterilizer selected from a plurality of differing types, each differing type of sterilizer carrying out a different sterilization cycle or different combination of sterilization cycles comprising, in combination
   a sterilizing chamber,
   conduit means connected to the chamber for delivering fluid to and from chamber to selectively establish fluid pressure conditions within the chamber,
   valve means for controlling fluid flow in the conduit means,
   such valve means being electrically operable,
   sensor means operatively associated with the chamber to be responsive to at least one chamber condition,
   electronic microcomputer controller means for controlling opening and closing of the valve means to selectively carry out a sterilizing cycle,
   the electronic microcomputer controller means comprising circuit board means,
   mounting means for mounting the circuit board means on the sterilizer, and
   connector means electrically interconnecting the electronic microcomputer controller means to the sensing means and the electrically operable valve means,
   the circuit board means having electronic components mounted on a plurality of individual circuit boards capable of operating such plurality of differing types of sterilizers with at least one circuit board mounting electronic components utilized on all types of sterilizers capable of being operated and being a complete microcomputer controller for at least one type of sterilizer 2. The apparatus of claim 1 wherein the circuit board which is a complete microcomputer controller for at least one type of sterilizer includes
   a microcomputer having memory means, low level input/output means, D.C. drive means, and A.C.

drive means, and wherein the remaining circuit board means includes additional memory means, additional input/output means, additional D.C. drive means and additional A.C. drive means.

3. The apparatus of claim 1 in which the plurality of sterilizing cycles comprises at least five separate sterilizing cycles including steam and biocidal gas sterilizing cycles.

4. The apparatus of claim 3 in which the plurality of differing types of sterilizers comprises at least five separate types of sterilizers including at least one sterilizer capable of carrying out differing steam sterilizing cycles and at least one sterilizer separately capable of carrying out a steam sterilizing cycle and a biocidal gas sterilizing cycle.

5. A sterilization apparatus to be identified as one of a plurality of differing types of sterilization apparatus, each different type carrying out a different stabilization cycle or a different combination of sterilization cycles, comprising
- a sterilization chamber,
- a plurality of valve means controlling conduits in operative association with the chamber for selectively admitting and removing fluid to and from the chamber,
- sensor means operatively associated with the chamber for sensing chamber conditions such as pressure and/or temperature,
- an electronic microcomputer controller means including circuit board means having a stored program for selectively controlling a cycle or combination of cycles which the apparatus to be identified can perform as well as cycles which can be performed by remaining differing types of sterilization apparatus,
- the electronic microcomputer controller means controlling the opening and closing of at least one valve means responsive to conditioning detected by the sensing means in accordance with such stored program, and
- means for automatically identifying the type of sterilization apparatus to such microcomputer controller means upon mounting of the circuit board means which provides electrical interconnection between such microcomputer controller means and the sterilization apparatus.

6. The apparatus of claim 5 in which the steps of a sterilization cycle may vary when performed by differing types of sterilization apparatus and wherein such microcomputer controller means is further responsive to such identification means to determine which steps to perform.

7. The apparatus of claim 5 wherein the means for automatically identifying the type of sterilization apparatus comprises
- means for determining electrical status of a plurality of conducting means, including
- means permanently fixed in the sterilization apparatus for establishing the electrical status of a predetermined one of such conducting means.

8. The apparatus of claim 7 including means for originating a signal at a circuit point and circuit path means connected between such circuit point and one of such plurality of conducting means for providing such signal at one of such conducting means,
- such circuit path means including such means permanently fixed in the sterilization apparatus.

9. The apparatus of claim 8 wherein each of such plurality of conducting means is connected to the one side of a voltage source with the remaining side of the voltage source being connected to ground, and the circuit path means includes means for switching a complete electrical circuit between ground and such one of such plurality of conducting means.

10. Sterilizer and control apparatus for selective operation of a sterilizer selected from a plurality of differing types of sterilizers, each differing type of sterilizer carrying out a different sterilization cycle or different combination of sterilization cycles comprising
- a sterilizer selected from such plurality of differing types of sterilizers, such selected sterilizer having a sterilizing chamber with conduit means and valve means for delivering fluid to and from the chamber and including sensor means operatively associated with the chamber to be responsive to at least one chamber condition,
- circuit board means including electronic components to which form an integrated microcomputer controller capable of controlling such plurality of differing types of sterilizers, such circuit board means having electronic components mounted on a plurality of individual circuit boards capable of operating such plurality of differing types of sterilizers with at least one circuit board mounting electronic components utilized on all types of sterilizers capable of being operated, and
- means electrically connecting the circuit board means to the sterilizer to carry out a sterilizing cycle capable of being performed by the selected sterilizer.

11. Sterilizer identification and control apparatus for any of a plurality of differing types of sterilizers, each differing type of sterilizer performing a differing sequence of operational steps, comprising, in combination
- an electronic controller programmed to selectively control such plurality of differing types of sterilizers,
- a sterilizer with chamber and associated structure for carrying out at least one sterilizing cycle, and
- means for interconnecting such controller and the sterilizer,
- such interconnecting means including electrically responsive structure which is separate for each differing type of sterilizer to be controlled so as to idenify the sterilizer with which such controller is interconnected.

12. Sterilizer control method providing for selective operation of a sterilizer selected from a plurality of differing types of sterilizers, each differing type of sterilizer carrying out a different sterilization cycle or different combination of sterilization cycles comprising
- selecting a sterilizer from such plurality of differing types of sterilizers, such selected sterilizer having a sterilizing chamber with conduit means and valve means for delivering fluid to and from the chamber and including sensor means operatively associated with the chamber to be responsive to at least one chamber condition,
- combining electronic components on circuit board means to form an integrated microcomputer controller capable of controlling such plurality of differing types of sterilizers, such circuit board means having electronic components mounted on a plurality of individual circuit boards capable of operating such plurality of differing types of sterilizers with at least one circuit board mounting electronic components utilized on all types of sterilizers capable of being operated, and electrically connecting the circuit board means to the sterilizer to carry out a sterilizing cycle capable of being performed by the sterilizer.

13. Sterilizer identification and control method for any of a plurality of differing types of sterilizers, each differing type of sterilizer performing a differing sequence of operational steps, comprising the steps of selecting a sterilizer from such plurality of differing types of sterilizers, such selected sterilizer including associated identification means which differentiate the selected sterilizer from remaining types of sterilizers of such plurality of differing types, assembling circuit board means to form an integrated electronic controller which is programmed to selectively control such plurality of differing sterilizers, and interconnecting such circuit board means and the sterilizer such that such associated identification means which is separate for each differing type of sterilizer automatically identifies the selected sterilizer to the controller.

* * * * *

UNITED STATES PATENT AND TRADEMARK OFFICE
CERTIFICATE OF CORRECTION

PATENT NO. : 4,261,950
DATED : April 14, 1981
INVENTOR(S) : Richard C. Bainbridge, Ronald P. Krahe It is certified that error appears in the above-identified patent and that said Letters Patent are hereby corrected as shown below:

Column 4, line 61, cancel "a".

Column 7, line 28, after "U-shaped", insert --frame--.

Column 8, line 19, after "416,", insert --418,--;
line 37, after "from", insert --the--.

Column 9, line 18, change "stabilization" to --sterilization--.

Signed and Sealed this

Fourth Day of August 1981

[SEAL]

Attest:

GERALD J. MOSSINGHOFF

Attesting Officer    Commissioner of Patents and Trademarks

UNITED STATES PATENT AND TRADEMARK OFFICE
CERTIFICATE OF CORRECTION

PATENT NO. : 4,261,950

DATED : April 14, 1981

INVENTOR(S) : Richard C. Bainbridge et al.

It is certified that error appears in the above—identified patent and that said Letters Patent is hereby corrected as shown below:

Column 10, line 21, cancel "to".

Signed and Sealed this

First Day of September 1981

[SEAL]

Attest:

Attesting Officer

GERALD J. MOSSINGHOFF

Commissioner of Patents and Trademarks

UNITED STATES PATENT AND TRADEMARK OFFICE
CERTIFICATE OF CORRECTION

PATENT NO. : 4,261,950
DATED : April 14, 1981
INVENTOR(S) : Richard C. Bainbridge et al.

It is certified that error appears in the above—identified patent and that said Letters Patent is hereby corrected as shown below:

Column 10, line 47, "idenify" should read -- identify --.

Signed and Sealed this

Seventeenth Day of November 1981

[SEAL]

Attest:

GERALD J. MOSSINGHOFF

Attesting Officer — Commissioner of Patents and Trademarks